United States Patent
Borberg et al.

(10) Patent No.: US 6,627,151 B1
(45) Date of Patent: *Sep. 30, 2003

(54) METHOD FOR TREATMENT DISEASES ASSOCIATED WITH A DETERIORATION OF THE MACROCIRCULATION, MICROCIRCULATION AND ORGAN PERFUSION

(76) Inventors: Helmut Borberg, Tulpenwg 19, 51427 Bergisch Gladbach (DE); Richard Brunner, IM Idienbachtal 28, 53474 Bad Neuenahr/Ahrweiler (DE); Michael Tauchert, Dudweilerstr. 19, 51375 Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/095,472

(22) Filed: Jun. 10, 1998

Related U.S. Application Data

(60) Provisional application No. 60/050,018, filed on Jun. 13, 1997, and provisional application No. 60/049,636, filed on Jun. 16, 1997.

(51) Int. Cl.$^7$ .......................... A61M 1/14; A61M 37/00; A61B 19/00; B01D 61/00
(52) U.S. Cl. ........................ 422/44; 604/4.01; 604/5.01; 604/5.04; 128/898; 210/651
(58) Field of Search ........................ 422/44; 604/4, 604/4.01, 5.01–5.04, 6.01, 6.04, 6.09; 210/650–52, 660, 663, 669, 679; 128/898; 514/802; 424/130.1, 140.1; 435/2, 283.1

(56) References Cited

U.S. PATENT DOCUMENTS

| | | | |
|---|---|---|---|
| 3,727,612 A | * | 4/1973 | Sayers et al. ............... 128/214 |
| 3,933,998 A | * | 1/1976 | Seidehamel et al. .......... 424/28 |
| 4,103,685 A | * | 8/1978 | Lupien et al. ............... 128/214 |
| 4,350,156 A | * | 9/1982 | Malchesky et al. ..... 128/214 R |
| 4,643,718 A | * | 2/1987 | Marten .......................... 604/4 |
| 4,685,900 A | * | 8/1987 | Honard et al. |
| 4,830,849 A | * | 5/1989 | Osterholm ..................... 424/2 |
| 4,900,720 A | * | 2/1990 | Kotitschke ................... 514/21 |
| 5,112,298 A | * | 5/1992 | Prince et al. ................... 604/6 |
| 5,171,456 A | * | 12/1992 | Hwang et al. ............... 210/782 |
| 5,277,820 A | * | 1/1994 | Ash ............................. 210/646 |
| 5,554,293 A | * | 9/1996 | Uhoch ......................... 210/650 |
| 5,649,903 A | * | 7/1997 | Deniega et al. ................ 604/4 |
| 5,753,227 A | * | 5/1998 | Strahilevitz ............... 424/140.1 |

(List continued on next page.)

OTHER PUBLICATIONS

Brunner, R.; Erythrocyte apheresis in combination with elimination of fibrinogen and plasma proteins of higher molecular weight in macular disease and in uveal effusion syndrome; Acta Med. Austriaca, 1991, spec. Issue 1, 63–65.*

Gavrilov, O; The assessment of the antithrombotic effectic of plasma and platelet apheresis as part of combined treatment for unstable angina; Kardiologiya; 28 (5), 60–64, 1988.*

(List continued on next page.)

*Primary Examiner*—Angela D. Sykes
*Assistant Examiner*—Patricia Bianco
(74) *Attorney, Agent, or Firm*—Needle & Rosenberg, P.C.

(57) ABSTRACT

The invention relates to a method for the effective treatment of diseases associated with a deterioration of the macrocirculation, microcirculation and organ perfusion to achieve an improvement of the local environment and the metabolic situation and to aim at the improvement of organ function or the stabilization of organ function with imminent functional deterioration, which comprises the treatment of blood of patients by extracorporeal plasmapheresis techniques.

3 Claims, 1 Drawing Sheet

U.S. PATENT DOCUMENTS

| | | | |
|---|---|---|---|
| 5,773,384 A | * | 6/1998 | Davankov et al. .......... 502/402 |
| 5,911,698 A | * | 6/1999 | Cham ............................ 604/4 |
| 5,919,369 A | * | 7/1999 | Ash ........................... 210/645 |
| 5,944,684 A | * | 8/1999 | Roberts et al. ................. 604/5 |
| 6,039,946 A | * | 3/2000 | Strahilevitz .............. 424/140.4 |
| 6,235,500 B1 | * | 5/2001 | Sligar et al. |
| 6,245,038 B1 | * | 6/2001 | Borberg et al. |

OTHER PUBLICATIONS

Georgadze et al., Plasmapheresis in the treatment of critical stages of ischemia in diabetic angiopathy of the lower extremities, Vestn Khir Im I I Grek, Mar.; 1989 142(3):20–4 (Medline Abstract).*

Brunner et al. "Clinical Efficacy of Haemorheological Treatment Using Plasma Exchange, Selective Adsorption and Membrane Differential Filtration in Maculopathy . . . " *Transfus. Sci.* 17(4):493–498, 1996.

Brunner et al. "Change in Hemorrheological and Biochemical Parameters Following Membrane Differential Filtration", *Intl. J. Artifical Organs* 18(12):794–798, 1995.

Brunner, Borberg et al. "Plasma Exchange and Immunoglobulins in the Treatment of Intermediate Uveitis", *Dev. Ophthalmol.*, Karger (Public.) Basel, vol. 23, p. 275–284, 1992.

Brunner, Borberg et al. "Erythrocyte Apheresis in Combination with Elimination of Fibrinogen and Plasma Proteins of Higher Molecular Weight in Macular Disease and in Uveal Effusion Syndrome", *Acta Medica Austriaca 18*, supplement 1, p. 63–65, 1991.

* cited by examiner

METHOD FOR TREATMENT DISEASES ASSOCIATED WITH A DETERIORATION OF THE MACROCIRCULATION, MICROCIRCULATION AND ORGAN PERFUSION

The present application claims priority from U.S. Ser. No. 60/050,018, filed Jun. 13, 1997 and from U.S. Ser. No. 60/049,636, filed Jun. 16, 1997.

BACKGROUND OF THE INVENTION

The present invention relates to a new method for the effective therapeutic treatment of diseases associated with a deterioration of the macrocirculation, microcirculation and organ perfusion to achieve an improvement of the local environment and the metabolic situation and to aim at the improvement of organ function or the stabilization of organ function with imminent functional deterioration.

The present invention relates especially to a new method for the effective treatment of cardiological and systemic diseases.

In the past ophthalmological diseases like age-related maculopathy (AMD) retinal vein occlusion, diabetic retinopathy, arterial occlusion, uveal effusion syndrome, NAION, Stargardt's-disease, uveitis, and maculopathy of different origin could not be treated with a generally accepted therapy. For example for the treatment of AM lasering treatments, radiation and operation were used. However these methods had no effect on the further development of the disease in many of the patients suffering therefrom. This principle has now been extended to cardiological diseases. Therapy refractory angina pectoris of coronary heart disease is the major disease. CHD is a severe progressive disease which occurs in the elderly. It is considered to be the most frequent cause of death in patients beyond an age of 65 years. There are more than 10 Million Americans suffering from this disease. An increasing number of patients after standard therapies such as coronary angioplasty, bypass operation and drug therapy are exhausted, demand new approaches. Extracorporeal haemorheotherapy (rheopheresis, rheo-apheresis) is a so far not considered or applied new treatment.

There is an increasing number of patients who underwent coronary angioplasty and/or coronary bypass surgery and are now again suffering from anginal pain due to the progression of the atherosclerotic disease. Even the new technique of transmyocardial laser revascularisation does not help them for more than 1–2 years. They then again depend on the conventional pharmacological therapy of coronary heart disease such as nitrates, beta-blockers and calcium antagonists, which become more and more ineffective during this stage of the disease. New types of antianginal medications are not expected to be developed during the next decade. As these patients finally have no therapeutic alternative in the very last stage of the disease, there is a great need for a new and effective therapeutic treatment of the above mentioned cardiological and systemic diseases.

In the early 90S the inventors of the present invention observed that the elimination of fibrinogen and plasma proteins of higher molecular weight led to an increase of the visual acuity of patients suffering from macular disease and uveal effusion syndrome (Brunner, Borberg et al. Acta Medica Austriaca 1991, 18, supplement 1, page 63 to 65). In this document 1 patient with uveal effusion syndrome and 16 patients with maculopathy were treated. The haematocrit was reduced by erythrocyte apheresis. Fibrinogen and plasma proteins were eliminated by plasma exchange using a solution of 5% human albumin. The visual acuity of 9 of the patients with maculopathy was significantly increased after one therapy.

In a further publication from 1991 (Brunner, Borberg et al., Dev. Ophthalmol., Karger (Public.) Basel, 1992, vol. 23, p. 275 to 284) it was studied whether clinical improvements could be obtained by plasma exchange therapy with patients suffering from intermediate uveitis using a solution of 5% human albumin. It was found out that both the haemorheological and immunomodulatory effects of this treatment could be beneficial in this disease. Human albumin as well as preserved serum were used as exchange fluids.

However, a general concept for the effective therapeutic treatment of cardiological diseases was not described in these documents.

Therefore it was the object of the invention to provide a method for the effective treatment of diseases associated with a deterioration of the macrocirculation, microcirculation and organ perfusion to achieve an improvement of the local environment and the metabolic situation and to aim at the improvement of organ function or the stabilization of organ function with imminent functional deterioration, especially for the effective treatment of cardiological and systemic diseases.

SUMMARY OF THE INVENTION

This object is solved by a method, which comprises the treatment of blood of patients by extracorporeal plasmapheresis techniques.

In a preferred embodiment the diseases are selected from the group comprising arterial occlusion, venous thrombosis, apoplexia, cerebral infarction, transitory iechasmic attack, multiple cerebral infarction syndrome, dementia, Alzheimer's disease, diabetes mellitus, burns, Septicaemia (Sepsis), Raynaud's syndrome, ulceration of the skin due to rheological alterations, ophthalmologic diseases especially maculopathy, retinal vein occlusion and uveal effusion syndrome, cardiologic and systemic diseases.

According to a preferred embodiment of the invention the cardiological and systemic diseases which can be treated are selected from the group comprising therapy refractory angina pectoris of patients with coronary heart disease, diseases of coronary microcirculation ("small vessel disease", "syndrome X"), disturbances of cerebral microcirculation (e.g. Morbus Binswanger), diabetic retinopathy, diabetic nephropathy, diabetic neuropathy, diabetic cardiomyopathy, pulmonary hypertension, artery occlusion, retinal vein occlusion.

In a further preferred embodiment the plasmapheresis technique is selected from the following techniques: blood cell plasma separation, plasma differential separation, plasma differential precipitation, plasma differential adsorption, plasma differential filtration.

The treatment comprises the steps of withdrawing the blood from the patient, treatment of the blood by the plasmapheresis techniques mentioned above and re-infusing the treated blood.

DETAILED DESCRIPTION OF THE INVENTION

Figure 1:
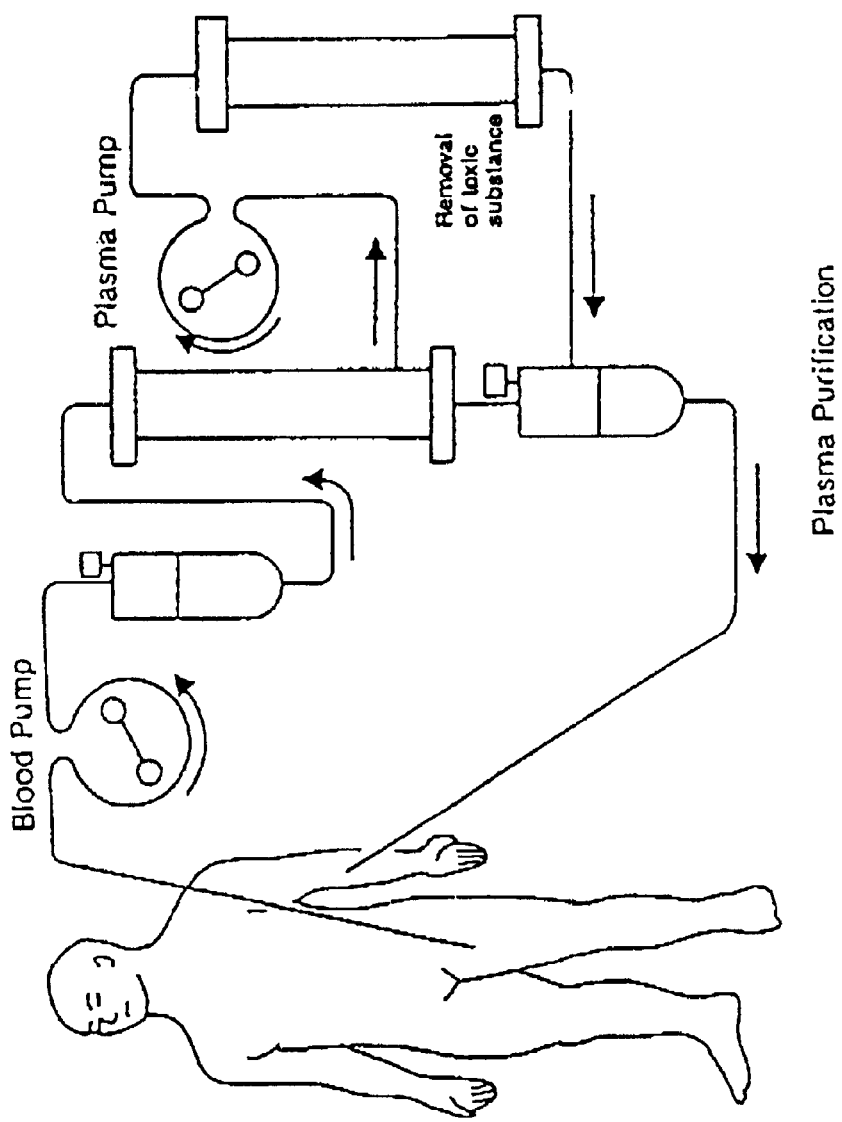
FIG. 1 is a schematic drawing of a patient connected to an extracorporeal system for plasmapheresis.

Hemapheresis (apheresis) is defined as the on line separation of blood into blood components. The process of separation refers to the blood cells or to the blood fluid (plasma). Haemapheresis procedures are performed using centrifugal or filtration techniques to modulate blood composition as for instance for the donation of blood components or to perform therapies. The modulation of the blood composition using hemapheresis procedures can generally be attributed to both elimination and dilution. The standard techniques are world wide distributed and under increasing usage.

Rheology is defined as follows. The fluidity of blood as a non Newtonian fluid is characterized from rheological parameters, mainly from viscosity. The viscosity of the blood in the human organism is determined from several variables, the most important being the concentration of blood cells and the protein content of the plasma. Within the plasma high molecular weight proteins, such as low density lipoprotein cholesterol, alpha-2-macroglobulin, immunoglobulin M, fibrinogen, are major determinants. Thus, hyperviscosity syndromes are mainly either due to hypercellularity as it occurs for instance in leukemias or due to an excessively elevated concentration of plasma proteins as for instance in Waldenström's disease. The treatment of diseases characterized from hyperviscosity has for many years been performed using haemapheresis techniques by removing such an excess of cells or plasma. These therapies are also generally known and world wide applied.

Cardiological diseases and the other systemic diseases mentioned are for unknown reasons hardly or not at all treated with haemapheresis techniques. Some of them, such as therapy refractory coronary heart disease are without a generally accepted therapy, though various attempts have without success been made to inhibit the progress of the disease. These failures may be due to therapeutic helplessness and also lack of knowledge on the pathogenesis of some of these conditions. Among several hypotheses one of them tries to relate the clinical deterioration with an insufficient and decreasing blood perfusion. All kinds of treatments used hitherto have the blood vessels as object of their direct or indirect target. Alternatively, an improvement of organ perfusion for instance due to an optimization of blood fluidity could well be used for the treatment of cardiological diseases associated with a disorder of the microcirculation.

According to the above mentioned theory it was assumed from the inventors, that a positive clinical effect might be observed in patients suffering from myocardial circulatory diseases and many other diseases of the microcirculation if the haemorheology could be improved following erythrocyte apheresis in combination with an elimination of fibrinogen and plasma proteins of higher molecular weight. Preliminary observations supported this hypothesis indeed, (R. Brunner, H. Borberg, J. Kadar, M. Reidel, K. Heidner, W. Konen. Erythrocyte apheresis in combination with elimination of fibrinogen and plasma proteins of higher molecular weight in macular disease and uveal effusion syndrome. AMA 1991; 18 (suppl. 1): 63–65). As a correction of the haematocrit is not often necessary, the studies concentrated more on an optimation of plasma viscosity applying plasma exchange against 5% human albumin (R. Brunner, H. Borberg, J. Kadar, A. Hoffmann, W. Konen, M. Heidel, K. Heidner, in Intermediate Uveitis, W R F Boke, K. F. Manthey, R. B. Nussenblatt (eds), Dev. Ophthalmol, Karger (publ.), Basel 1992; 23; 275–284. These observations were also supported from preliminary observations in cardiological diseases such as refractory angina pectoris in end-stage coronary heart disease. (M. Tauchert, A. Sonntag, B. Weidmann, A. Gaczkowski, R. Brunner, H. Borberg: Extracorporeal hemorheotherapy of refractory angina pectoris. Jpn. J. Aphe-resis 1997; 16, 1: 35–37)

Subsequently, several plasma differential separation techniques were investigated and compared with plasma exchange therapy. It could be shown, that plasma viscosity, standardized whole blood viscosity at an hct of 0.45 and standardized erythrocyte aggregation at an hct of 0.30 were still significantly decreased one day after therapy. The values of the standardized whole blood viscosity showed a non-linear, haematocrit-dependent rise, whereas the erythrocyte aggregation revealed the maximum value near a haematocrit of 0.3. A reduction in all adjusted haematocrits was demonstrated. Also, native whole blood viscosity and erythrocyte aggregation were lowered within the same range while the haematocrit was only slightly diminished. The high molecular weight substances of the plasma (Lipids such as total cholesterol, LDL-cholesterol, RDL-cholesterol, proteins such as alpha-2-macroglobulin, immunoglobulin including fibrinogen) were decreased between 20–70% (R. Brunner, R. A. Widder, P. Walter, B. Borberg, K. Oette. Change in haemorheological and biochemical parameters following membrane differential separation. Int. J. Artif. Organs 1995: 18, 12:794–798).

Finally, several plasma differential separation techniques were examined from the inventors to improve the techniques applicable for an extracorporeal haemorheotherapy of ophthalmological diseases. Techniques applicable for the use within the invention consist of blood cell—plasma separation, also named primary separation, plasma differential separation, also named secondary separation. After the process of separation and elimination of either cells (if necessary) and/or plasma proteins whole blood is returned to the patient. However, these techniques are not obligatory, as whole blood perfusion of filters or adsorbers may also be applied.

Blood #ell—Plasma Separation (Primary Separation)

Centrifugal separation based on continuous or discontinuous flow principles (e.g. IBM model 2997, COBE Spectra, FRESENIUS AS 104, DIDECO Excel, HAEMONETICS model 50), can successfully be applied to separate blood cells from blood plasma. Alternatively flat sheet membrane (COBE TPE) or hollow fiber plasma separators (ASAHI OP—05) were and can be used to obtain cell free plasma. The separated plasma is discarded to be substituted with human albumin, a mixture or combination of human albumin with other fluids or other fluid alone (plasma exchange therapy).

For anticoagulation usually heparin, citrate or a combination of both may be applied. Other upcoming anticoagulation procedures are equally applicable. The access to the circulation can be established on a veno-venous basis from one antecubital vein to the other or from a central venous access to a peripheral vein or using an artificial access to the circulation applying for instance a shunt, a Shaldon catheter or any other catheter using for instance Seldinger's technique. Single needle techniques may also be used.

Plasma Differential Separation (Secondary Separation)

As plasma exchange therapy may be characterized from safety drawbacks as for instance the transfer of infectious agents such as viruses or prions, secondary or plasma differential separation techniques are preferred. They consist of plasma differential precipitation with heparin, adsorption or absorption of plasma proteins or plasma filtration. All technologies for secondary plasma separation are preferably applied on-line.

Plasma Differential Precipitation

Plasma differential separation is performed adding an excess of heparin to the separated plasma, establishing an $p_H$ of 5.12 to precipitate heparin binding plasma proteins, separating the precipitate from the plasma by hollow fiber filtration, and removing the heparin excess via adsorption. Any other plasma protein precipitating technique may also be applied.

Plasma Differential Adsorption

Plasma differential separation is performed permitting the separated plasma to pass through an adsorption column eliminating plasma proteins for instance using hydrophobic inter action chromatography (applying for instance an ASAHI TR 350 adsorption column) or affinity chromatography (applying for instance an LDL-apheresis column) or any other related adsorption technology. (As mentioned above, instead of perfusing adsorption columns with separated plasma, whole blood perfusion in biocompatible systems may also be applied).

Plasma Differential Filtration

Plasma differential separation is performed permitting the separated plasma to pass through a secondary filter eliminating plasma proteins according to the pore size of the membranes (for example ASAHI AC 1730, ASAHI AC 1760, ASAHI Rheofilter 2000, ASAHI AC 1770, KURARAY Evaflux filters with different pore sizes, DIDECO Albusave).

Retransfusion

If whole blood perfusion is used, the blood cleared from the eliminated components is returned to the patients. If plasma differential separation is used, the blood components without the calls and/or plasma are returned to the patient.

A typical example of plasma differential separation using filtration as an example is shown in FIG. 1. (Step 1: Blood is removed from a pump into the extracorporeal circuit, where cells are separated from the plasma in a plasma separator. The plasma separator may consist of either a centrifugal or a filtration apparatus. Step 2: The separated plasma is either discarded and replaced (plasma exchange), or, alternatively, permitted to pass through one or more secondary devices eliminating the precipitated, adsorbed or filtered plasma. Step 3: The purified blood is returned to the patient. Note that whole blood perfusion devices are correspondingly simpler).

Treatments were performed processing about 50 to 200% of the patient's plasma volume preferably 120% on day one and about 50 to 150% preferably 60–80% of the patient's plasma volume on day 3 or 4 with either technique described above. Blood samples were drawn prior to and one day after the second treatment to measure the efficacy parameters. Two treatments were considered as one cycle. The interval from one cycle to another was generally 4–5 weeks. A total of 5 treatment cycles was applied.

Other treatment approaches mainly but not only used for maintenance therapy consisted of a single treatment or one single treatment at different intervals. The definition of the interval is related to the choice of the separation techniques, thus other approaches are equally possible.

Patients, who were treated with a method according to the invention reported about daily life improvements such as a reduced number of heart attacks, an improved work capacity, better social contacts and an increased degree of independence.

The present invention will be further understood by reference to the following examples.

EXAMPLES

Example 1
Treatment of Patients With Therapy Refractory Angina Pectoris (n=10).

The mean age of these patients was 63±5 years. All had undergone maximum pharmacological treatment, eight of them coronary bypass surgery, two of the latter even transmyocardial laser revascularisation (TMLR).

For these patients with therapy refractory angina pectoris treatment consisted of two treatment sessions with a one day interval (1 treatment cycle). The patients were hospitalized for 5 days. Measurements were carried out one day prior to the first treatment session and 24 hours after the second treatment session. The mean duration of treatment was 28 months, the mean interval between the double treatment sessions (treatment cycles) was 6 weeks.

We applied the following extracorporeal treatment procedures: plasma exchange with 5% human albumin solution, selective adsorption using the trytophan-polyvinylalcohol adsorber TR-350 (Asahi Medical Tokyo) and membrane differential separation with the Cascadeflo AC-1760 (Asahi Medical Tokyo). The amount of plasma volume perfused varied between 80–120% of the patient's plasma volume. A centrifugal blood separator (IBM 2997, Cobe Spectra) and the OP-05 hollow fiber filter (Asahi Medical Tokyo) were used for primary separation. The blood flow was established between two antecubital veins. Anticoagulation consisted of heparin (2500 units) injected as a bolus prior to therapy and ACD-A citrate continuously infused at a ratio of 1:16 during the course of treatment. Patients with severe systemic diseases like malignomas, cardial decompensation, hepatitis, HIV infection as well as severe hypotony were excluded. Plasma and standardized, whole blood viscosity at a haematocrit of 45% were measured using a coneplate system (CS-Rheometer Carri Med Ltd., Dorking, UK) at 37 degrees Celsius and standardized erythrocyte aggregation at a haematocrit of 30% was measured applying the Mini-Aggregometer (Myrenne GmbH, Roetgen, Germany) (7).

Clinical parameters for the evaluation of the efficacy of the extracorporeal hemorheotherapy were the number of anginal attacks per day (plotted in a protocol book), frequency of nitroglycerin applications and dosage per day (plotted in a protocol book) and work capacity (W×min) as determined by bicycle ergometry.

Results

Severe side effects did not occur. Two patients experienced hypotonic episodes with a drop of blood pressure not below 90/60 mmHg. They were treated with the substitution of 250 ml 5% human albumin. No further medical treatment was required.

Biochemical Parameters

Fibrinogen as, one of the most important factors of plasma viscosity was decreased from 3,61±0,16 g/l prior to the first treatment to 1,81±0,09 after the first double procedure. Prior to the last treatment performed the value was 3.05±0.11 g/l and decreased due to the procedure to 1.71±0.09 g/l.

Total protein was only affected slightly from extracorporeal rheotherapy (6,83±0,09 g/dl before and 5,72±0,07 g/dl after the first procedure, 6,82±0,1 g/dl prior to and 5,95±0,04 g/dl following the hitherto last intervention.

Immunoglobulin M (IgM) decreased from 142,4±5,8 mg/dl to 103,1±6,8 mg/dl during the first treatment; the values before and after the hitherto last therapy were 143, 8±8,9 mg/dl and 85,3±4,0 mg/dl correspondingly.

Immunoglobulin A (IgA) was influenced to a similar extent (143,5±7,9 mg/to 124,3±4,1 mg/dl prior to and after the first therapy resp. 163,4±1,9 mg/dl to 94,4±8,9 mg/dl before and after the hitherto last therapy.

Immunoglobulin G (IgG) decreased from 992,2±71,2 mg/dl to 879,1±52,3 mg/dl during the first and from 1010, 5±91,5 mg/dl to 702,1±149,2 mg/dl during the last treatment. The decrase of immunoglobulins due to the Theological therapy was obviously not substantial enough to lead to any infection whatsoever.

There was no significant effect on the hematocrit (41, 0±0,9 % resp. 41,7±0,9% during the first intervention; 41,8±0,6% resp. 42,3±0,6% during the last treatment).

The number of platelets remained nearly unchanged from the treatments (215,3±6,3×$10^3$ per microliter resp. 213,1±5, 1×$10^3$ during the first treatment and 207,0±4,5×$10^3$ resp. 207,9±6,0×$10^3$ per microliter during the last procedures).

Low density lipoprotein cholesterol (LDL-C) was reduced from 127,2±17,0 mg/dl to 71,1±11,2 g/dl within the first therapy. The effect of the second treatment was similar (122,8±16,0 mg/dl to 59,0±7,2 mg/dl). Lipoprotein (a) was influenced similarly (89.1±6.8 mg/dl to 45.0±8.0 mg/dl resp. 93.9±51.0±5.1 mg/dl). The decrease of the lipoproteines under apheresis is a considerable contribution to the alteration of the plasma viscosity.

Clinical Results

Attacks of Angina Pectoris

The number of angina pectoris attacks per day was reduced due to the rheological treatment from 5,7±0,4 to 2,3±0,3 following the first treatment and from 4,5±0,3 to 1,8±0,3 by the hitherto last treatment procedure. Some patients were completely free from anginal pain for the first days or even weeks after therapy. During the last third of the interval between the therapeutic procedures (4–9 weeks with a mean of 6 weeks), the number of angina pectoris attacks rose again. The therapy was repeated, when the frequency and intensity of attacks was nearly the same as before therapy.

Dosage of Nitroglycerin

The number of nitroglycerin applications (and thus the daily dosage) was reduced due to the apheresis from 3,8±0,3 to 1,7±0,3 after the first treatment. Prior to the hitherto last rheoapheresis treatment the number or daily doses was 2,9±0,4 and was reduced to 1,2±0,2.

Work Capacity

Work capacity as determined using bicycle ergometry is a reliably reproducible paramter if the measurements are always performed during the same daytime and under otherwise identical conditions. The patient starts the ergometry with a standard minimal load (generally 50 Watt) and terminates it with the onset of angina pectoris and/or exhaustion. The time from start to stop multiplied with the work load represents the individual work capacity. Work capacity was increased from 209±22 W×min from prior to the first treatment to 369±27 W×min after the hitherto last therapy.

Discussion

The concentration of high molecular weight substrates in the plasma is a major determinant of the plasma viscosity and thus whole blood viscosity. The intensity and duration of a diminuition of such substrates due to plasma differential separation used for rheotherapy is superior to other rheological treatments such as isovolaemic haemodilution or the application of urokinase. The application of this innovative concept of extracorporeal haemorheotherapy to 10 patients with therapy refractory angina pectoris without treatment alternative performed over a period of 28 months demonstrated both safety and efficacy in this group of seriously sick patients. The therapeutic effect decreased or eliminated the patients complaints, increased their quality of life and has a life prolongating effect.

Though an interval of six weeks was appropriate for most of the patients it is necessary to individualize it according to the laboratory (mainly the clinical-chemical and hemorheological) and clinical data of the patient.

Example 2

Treatment of Patients With Disorders of the Microcirculation for Instance "Small Vessel Disease", "Syndrome X" (n=3)

The etiology and pathogenesis of so named "small vessel disease" or "syndrome X" are unknown. The syndrome is characterized by angina pecoris and positive stress tests however angiographically normal epicardial coronary arteries and slow coronary blood flow. There is, however, evidence of structural and functional alteration of prearteriolar myocardial blood vessels with a severely reduced vasodilator reserve due to endothelial dysfunction. Extracardiac symptoms such as migraine, pathological pain perception, neuro-regulatory abnormalities and a reduced vasodilator reserve of the forearm hinto to a systemic disease. A high prevalence of pathological brain SPECT examinations in patients with cardiac "syndrome X" supports the hypothesis of a generalized vascular disorder (B. Weidmann, W. C. Jansen, A. Bock, J. Assheuer, M. Tauchert. Technetium—99 m—HMPAO brain SPECT in patients with syndrome X. Am. J. Cardiol. 1997; 79: 959–961.

3 patients (56±10 years of age) with "syndrome" as documented by exercise test, characteristic blood flow in angiographically normal coronary arteries, angina pectoris under stress and pathologic brain SPECT were treated with extracorporeal hemorheotherapy using differential filtration over a period of 31 months at intervals of 3–8 (mean 6) weeks. The biochemical parameters complied with those demonstrated in example 1. Clinical test parameters followed for evaluation were the number of angina pectoris attacks per day, the number of daily applied nitroglycerin applications, the work capacity and the symptoms of cerebro-vascular insufficiency as described from the patients.

Results

The biochemical parameters were influenced from the extracorporeal hemorheotherapy the same way and extent as described in example 1 for patients with refractory angina pectoris with severe, progressed coronary heart disease.

The number of anginal attacks per day was reduced from 6,3 to 2 following the first treatment and from 5,9 to 2,0 by the hitherto last therapeutic procedure.

The frequency of nitroglycerin applications per day decreased from 5.0 to 1,5 as related to the first treatment and from 4,8 to 1,4 to the hitherto last therapy.

The work capacity rose from 189 W×min to 333 W×min under the first apheresis application and from 201 W×min to 349 W×min to the hitherto last treatment.

The symptoms of cerebrovascular insufficiency (forgetfulness, fatigue, reduced vigilance) were considerably improved.

Conclusions

"Syndrome X" of the heart is well known as a syndrome with angina pectoris, positive stress tests and slow flow in angiographically normal epicardial coronary arteries. Some pathogenetic findings indicate, that "syndrome X" of the heart is the first expression of a microvascular disease of systemic character, appearingly due to endothelial dysfunction. Any efficacious therapy was so far unknown. The therapeutic effects observed in the group of patients described indicate that the alteration of the plasma and whole blood viscosity as obtained by extracorporeal haemorheotherapy is a therapeutically useful treatment approach.

Example 3

Treatment of Diabetes Mellitus
Treatment of Patients With Diabetic Gangrene of the Foot (n=4)

Micro- and macroangiopathy of the whole arterial system are very common in patients with a history of long lasting diabetes mellitus. Among other complications stroke, myocardial infarction, diabetic cardiomyopathy, diabetic renal failure, diabetic retinopathy, diabetic neuropathy or gangrene of the toes and feet are common.

In the late stage of diabetic angiopathy leading for instance to gangrene of the foot due to ischaemia, there is up to now no effective treatment available. Thus surgical amputation of necrotic toes, the forefoot or forefeet or finally of the whole foot are necessary after gangrene appeared.

Four patients (66±5 years of age) with beginning gangrene of toes or parts of their feet were treated with extracorporeal haemorheotherapy in the same manner as described before. The following prerequisites were fulfilled:

1. Long lasting diabetes mellitus
2. Plasma fibrinogen higher than 5.0 g/l
3. No further treatment alternative due to exhaustion of conventional antiischemic therapy including vascular surgery and intraarterial infusions.
4. Beginning gangrene
5. Indication for surgical amputation as given from an experienced vascular surgeon Results All four patients demonstrated an improved perfusion of the gangrenous areas ready following the first therapeutic session. After three treatment cycles (six single therapies), any need for further surgical intervention was denied from both, the vascular surgeon and the patient.

What is claimed is:

1. A method of treating small vessel disease of a heart in a subject diagnosed with small vessel disease of the heart, comprising the steps of withdrawing blood from the subject, treating the blood by plasmapheresis, and reinfusing the treated blood into the subject, thereby treating the small vessel disease of the heart.

2. A method of treating small vessel disease of a heart in a subject diagnosed with small vessel disease of the heart, comprising the steps of withdrawing blood from the subject, treating the blood by removing high molecular weight protein, and reinfusing the treated blood into the subject, thereby treating the small vessel disease of the heart.

3. The method of claim 2, wherein the high molecular weight protein is selected from the group consisting of fibrinogen, low density lipoprotein cholesterol, alpha-2-macroglobulin and a mixture thereof.

* * * * *